(12) United States Patent
Hochberg et al.

(10) Patent No.: US 7,985,580 B2
(45) Date of Patent: Jul. 26, 2011

(54) APPARATUS FOR THE PRODUCTION OF ALCOHOL

(75) Inventors: Ulrich Hochberg, Karlsruhe (DE); Matthias Schormueller, Karlsruhe (DE)

(73) Assignee: GEA Wiegand GmbH, Ettlingen (DE)

( * ) Notice: Subject to any disclaimer, the term of this patent is extended or adjusted under 35 U.S.C. 154(b) by 1227 days.

(21) Appl. No.: 10/532,117

(22) PCT Filed: Oct. 20, 2003

(86) PCT No.: PCT/EP03/11602
§ 371 (c)(1),
(2), (4) Date: Apr. 21, 2005

(87) PCT Pub. No.: WO2004/038031
PCT Pub. Date: May 6, 2004

(65) Prior Publication Data
US 2005/0266539 A1    Dec. 1, 2005

(30) Foreign Application Priority Data
Oct. 21, 2002 (DE) .................................. 102 49 027

(51) Int. Cl.
*C12M 1/00* (2006.01)
*C12M 3/00* (2006.01)

(52) U.S. Cl. .................... 435/289.1; 435/291.1; 426/11; 426/16; 426/18; 203/18; 203/19

(58) Field of Classification Search ................ 435/289.1
See application file for complete search history.

(56) References Cited

U.S. PATENT DOCUMENTS

| | | | | |
|---|---|---|---|---|
| 2,225,428 A | * | 12/1940 | Christensen | 426/624 |
| 2,343,706 A | * | 3/1944 | Reich | 435/93 |
| 3,443,958 A | * | 5/1969 | Dennis et al. | 426/29 |
| 3,968,739 A | * | 7/1976 | Stoltenburg | 99/276 |
| 4,287,304 A | * | 9/1981 | Muller et al. | 435/162 |
| 4,309,254 A | * | 1/1982 | Dahlstrom et al. | 203/47 |
| 4,328,317 A | * | 5/1982 | Prentice et al. | 435/294.1 |
| 4,407,662 A | * | 10/1983 | Ginder | 95/105 |
| 4,617,270 A | | 10/1986 | Anderson et al. | |
| 5,545,543 A | | 8/1996 | Zinnamosca et al. | |

FOREIGN PATENT DOCUMENTS

DE    31 15 289 A1    5/1982
(Continued)

OTHER PUBLICATIONS

W. P. Jarowenko "Tekhologija spirta", Moskau, Kolos, Kolos-Press, 2002, pp. 97-111, 186-193, 314-319.

*Primary Examiner* — William H Beisner
*Assistant Examiner* — Danielle Henkel
(74) *Attorney, Agent, or Firm* — Rothwell, Figg, Ernst & Manbeck, P.C.

(57) ABSTRACT

The aim of the invention is to produce alcohol from plant-based raw materials while reducing energy consumption. Said aim is achieved by separating the husk portion of cereals during grinding and feed said husk portion to a dryer (21) which dries distiller's wash as a carrier medium for distiller's wash. The lost heat of said dryer (21) is supplied to the distillation station (15) as process heat. The lost heat of a molecular sieve (45) that drains the raw alcohol is also redirected to the distillation station (15) as process heat.

43 Claims, 4 Drawing Sheets

FOREIGN PATENT DOCUMENTS

| | | |
|---|---|---|
| DE | 32 04 910 A1 | 12/1982 |
| DE | 30 37 736 C2 | 1/1984 |
| DE | 32 04 910 C2 | 3/1990 |
| DE | 31 45 812 C2 | 1/1992 |
| DE | 31 42 518 C2 | 10/1992 |
| EP | 0 052 352 A1 | 5/1982 |
| EP | 0 098 332 A1 | 1/1984 |
| WO | WO 83/01627 A1 | 5/1983 |
| WO | WO 96 36723 A | 11/1996 |
| WO | WO 01/02535 A2 | 1/2001 |

* cited by examiner

APPARATUS FOR THE PRODUCTION OF ALCOHOL

CROSS REFERENCE TO RELATED APPLICATION

This application is a 35 USC §371 National Phase Entry Application from PCT/EP2003/011602, filed Oct. 20, 2003, and designating the United States.

DESCRIPTION

The invention relates to an apparatus for the production of alcohol from carbohydrate- or sugar-containing raw material.

The industrial production of alcohol, in particular ethyl alcohol, from carbohydrate- and/or sugar-containing plant raw materials by conventional methods of liquefaction of the raw material, fermentation to form a mash and subsequent distillation of the crude alcohol is energy-consuming, in particular when the vinasse produced as residue in the distillation is dried for producing animal feed or the like.

Thus, for example, to produce one liter of anhydrous ethyl alcohol and dried vinasse requires between 7 and 8 kg of steam. In total, the energy required for the alcohol production exceeds in conventional processes the energy content of the alcohol and accordingly, the use of alcohol as fuel in machinery, for example car engines, is unprofitable based on the total energy balance.

It is an object of the invention to indicate a way as to how alcohol, in particular ethyl alcohol, and dried vinasse can be produced from plant raw materials with less energy expenditure than hitherto.

The invention starts from a conventional apparatus for the production of alcohol from plant raw materials which comprises:
a fermentation station fermenting liquefied raw material to mash,
a distillation station separating off the alcohol from mash and
a drying station for the vinasse produced in the distillation station.

For the invention, a plurality of aspects are critical, which each on their own and certainly in their combination make possible considerably less costly production of the alcohol, in particular ethyl alcohol, from carbohydrate- and/or sugar-containing plant raw materials, for example corn, wheat, sorghum or else molasses. Alcohol and dried vinasse may be produced using considerably less energy, in particular less than 50%, of the energy expenditure hitherto.

From a first aspect, the problem underlying the invention in the production of alcohol from cereals, for example corn or wheat or the like is solved by the means that a milling station milling to flour the cereal kernel comprising the starch and/or the sugar with removal of at least a part of the seed coat portions surrounding the kernel, and a liquefaction station digesting the flour are provided, and that the removed seed coat portions can be fed to the drying station as carrier medium for the vinasse drying. Even though a certain percentage of the fermentable carbohydrates or sugar contents of the raw material are not also fed to the fermentation process together with the seed coat portions produced as bran or the like, this circumstance is compensated for by the fact that the mash is richer in fermentable carbohydrates and sugar, so that higher-percentage alcohol can be distilled. At the same time the energy consumption in the distillation station is decreased.

In conventional driers used for vinasse drying, a portion of the dried vinasse is recirculated as carrier material to the drying process. This portion, in the context of the invention, can be decreased or omitted entirely, after, as carrier medium, the seed coat portions (husks or bran) removed in the milling are fed directly to the drier. Since the removed seed coat portions are not fed to the liquefaction, that is to say do not need to be dried, the energy consumption of the drier decreases, and smaller driers than hitherto can be used.

In order to be able to remove the seed coat portions adequately in the milling station, expediently a roller mill or impact jet mill is used. A weight ratio of the seed coat portions of the removed seed coat portions to the flour of 1:9 to 2:8 has proved to be an optimum between improvement of the drying process on the one hand and adequate alcohol yield on the other. The mean particle size of the cereals milled in the milling station should be greater than 0.2 mm and is expediently between 0.5 mm and 1 mm.

In the production of alcohol, the generally granular starch present in the plant raw material must be liquefied or digested. Customarily this is performed with addition of enzymes by steam which heats the flour, or if appropriate flour present in a suspension, above its gelatinization temperature determined by the raw material. After a residence time period permitting the enzymatic liquefaction, the "sweet mash" produced in the liquefaction step must be cooled again. If appropriate, a pre-fermentation step or saccharification step can follow the liquefaction step.

In the case of conventional liquefaction stations, the starch is heated in a single step to above the gelatinization temperature by steam via a steam jet heater charged with live steam. For the liquefaction in this case, a comparatively large amount of energy is required.

From a second aspect, the energy requirement of the liquefaction station may be considerably decreased if the liquefaction station comprises a mixing condenser which admixes steam to the product stream of the comminuted raw material or a suspension thereof and comprises at least one mixing stage, and also a steam-jet injector which is downstream of the mixing condenser and admixes hot steam to the product stream, and an expansion cooler for the product stream which is downstream of the steam-jet injector and comprises at least one expansion stage. The mixing condenser admixes the expansion steam of the expansion cooler with the product stream, that is to say utilizes the energy recovered from the product stream in the expansion cooler for the partial heating of the product stream in the liquefaction. In a preferred embodiment, the mixing condenser heats the product stream to a temperature below the gelatinization temperature of the raw material, so that the steam-jet injector need only further feed heating energy, for example from live steam, for the residual heating to above the gelatinization temperature. Comparatively little energy is required for this residual heating step.

At least the expansion cooler is preferably of multistage construction, the mixing condenser admixing to the product stream at least the expansion steam from the first expansion stage of the expansion cooler. The expenditure in terms of apparatus is comparatively low if the mixing condenser is at the single-stage construction and the expansion cooler is of two-stage construction. The expansion steam of the second stage of the expansion cooler can also be recovered for process purposes.

The process exploits the fact that the gelatinization temperature at which the liquefaction of the starch of the raw material begins is of the order of magnitude of 90° C., while for the subsequent saccharification, only about 60° C. is required, that is to say the fermentation temperature of the subsequent mashing is only 35 to 40° C. During the residence time to be maintained for the enzymatic liquefaction, which can be between some minutes and about one hour, heat losses can be prevented by suitable insulation measures. A particular advantage of the use of a mixing condenser heated by expansion vapors is that no heat transfer surfaces are provided which, in conventional liquefaction processes, have a tendency to form encrustations.

In the fermentation, in addition to alcohol, carbon dioxide ($CO_2$) is also produced, which is partly dissolved in the mash. The $CO_2$ dissolved in the mash, however, impedes the function of the distillation columns of the distillation station and sometimes requires complex constructions, in particular since the fermented mash foams if the $CO_2$ dissolved thereinbefore escapes. Not least, the $CO_2$ escaping in the distillation column increases the pressure drop in the distillation column.

In a third aspect of the invention, the expenditure in terms of apparatus of the distillation station can be reduced if, between the fermentation station and the distillation station, a degassing station is disposed in which the mash product stream passes from top to bottom through a vertical tube bundle evacuated at its bottom end and expands in the tube bundle. The resultant steam pulverizes the mash foam in the tube bundle so that the distillation columns can be built more simply. In addition, the vacuum system of the distillation column is simplified. The degassing process is reinforced if the mash product stream, before entry into the tube bundle, passes through a heat exchanger which preheats the mash. In addition, the mash is brought here closer to the distillation temperature.

Customarily, distillation columns are heated by live steam. In a fourth aspect, the invention demonstrates a way in which it is possible to utilize energy already being produced elsewhere in the alcohol production apparatus for heating the distillation column. For this it is provided that the drying station comprises a drier finally drying the vinasse having a dew point temperature of above 95° C., preferably 100° C. to 105° C., and that the distillation station has a distillation column heated by the exhaust steam of the drier. The exhaust steam of such a drier may heat exclusively at least the distillation column delivering the crude alcohol, in particular if this distillation column does not have excess pressure drops, as may be achieved, as explained hereinbefore before, by the $CO_2$ degassing of the mash fed to this distillation column. High dew point temperatures of the exhaust gas may be achieved especially using a drier which generates essentially air-free exhaust steam. Such a drier can be constructed, for example, as a superheated steam drier operated with superheated steam.

Hereinbefore before it has been explained how, by separating off the seed coat portions in the case of cereals as raw material of alcohol production, the drier can be made smaller. In some circumstances, this size reduction of the drier leads to the fact that it cannot as such produce sufficient waste steam energy for heating the distillation column. A fifth aspect of the invention indicates a way in which further heat energy for heating the distillation column can be recovered from process heat to be employed for this purpose in any case.

It has been found that the residual energy of the alcohol dehydrated in a dehydration station is sufficient to compensate for any energy deficit of the distillation station. In a fifth aspect of the invention it is provided that the distillation station has a first distillation column which is heated in particular by exhaust steam of the drying station, to which distillation column is connected a dehydration station dehydrating its crude alcohol product stream and that, at an intermediate level of the first distillation column above its mash feed level, a second distillation column is connected which is heated via a heat exchanger with heat of the dehydrated alcohol vapor of the dehydration station.

In a "side stripper" arrangement of this type, in the second distillation column, alcohol is no longer distilled off from mash, but is separated off from an alcohol-water substrate with correspondingly reduced distillation energy.

In a preferred embodiment, the heat exchanger assigned to the second distillation column is constructed as a falling-film evaporator heated by dehydrated alcohol vapor of the dehydration station to which is fed in the circuit first runnings water from the bottom of the second distillation column for the dehydration. The alcohol-water substrate which is recirculated from the second distillation column to the first distillation column is accordingly alcohol-richer than the substrate fed to the second column from the first distillation column.

The dehydration station is preferably a molecular sieve to which the crude alcohol is fed, if appropriate after a preheating, at a higher pressure than customary, in particular at a pressure of greater than 1.7 bar absolute, if the molecular sieve is operated at such an elevated pressure, waste heat temperatures of the dehydrated alcohol vapor of about 90° C. may be achieved and, as described hereinbefore before, used for heating the heat exchanger which is preferably constructed as a falling-film evaporator.

The concept of using the residual heat of the dehydrated alcohol product stream at another place in the process sequence may be implemented in another way, for example to improve the efficiency of the vinasse drying. In a sixth aspect it is provided that the drying station comprises a separator, for example a decanter or the like, which separates the vinasse into a vinasse-thin juice product stream and a vinasse-solids product stream, and also an evaporator which concentrates the vinasse-thin juice product stream by evaporation to form vinasse thick juice. The drying station further comprises a drier which finishes the drying of the vinasse-thick juice together with the vinasse-solids to give dry vinasse. So if a dehydration station is here also connected downstream of the distillation station, which dehydrates its crude alcohol product stream, at least one evaporator stage of the evaporator evaporating the vinasse-thin juice product stream can be heated with heat of the alcohol vapor dehydrated in the dehydration station.

For example, the evaporator can be of two-stage construction and comprise a pre-evaporator and an end evaporator, the end evaporator then being heated with dehydrated alcohol vapor from the dehydration station. The pre-evaporator is expediently of a size such that it preconcentrates the influent vinasse thin juice to a solids concentration of 17% to 24%, while the end evaporator thickens this preconcentrate to give thick juice (syrup) having a solids content of, for example, 25 to 50%, depending on raw material and enzymes added.

Under the last-mentioned aspect also, the dehydration station is preferably constructed as a molecular sieve to which is fed the crude alcohol which is dehydrated and if appropriate preheated to above 90° C. at a pressure of greater than 1.7 bar absolute.

The invention will be described in more detail hereinafter on the basis of a drawing. In the drawing.

Figure 1:
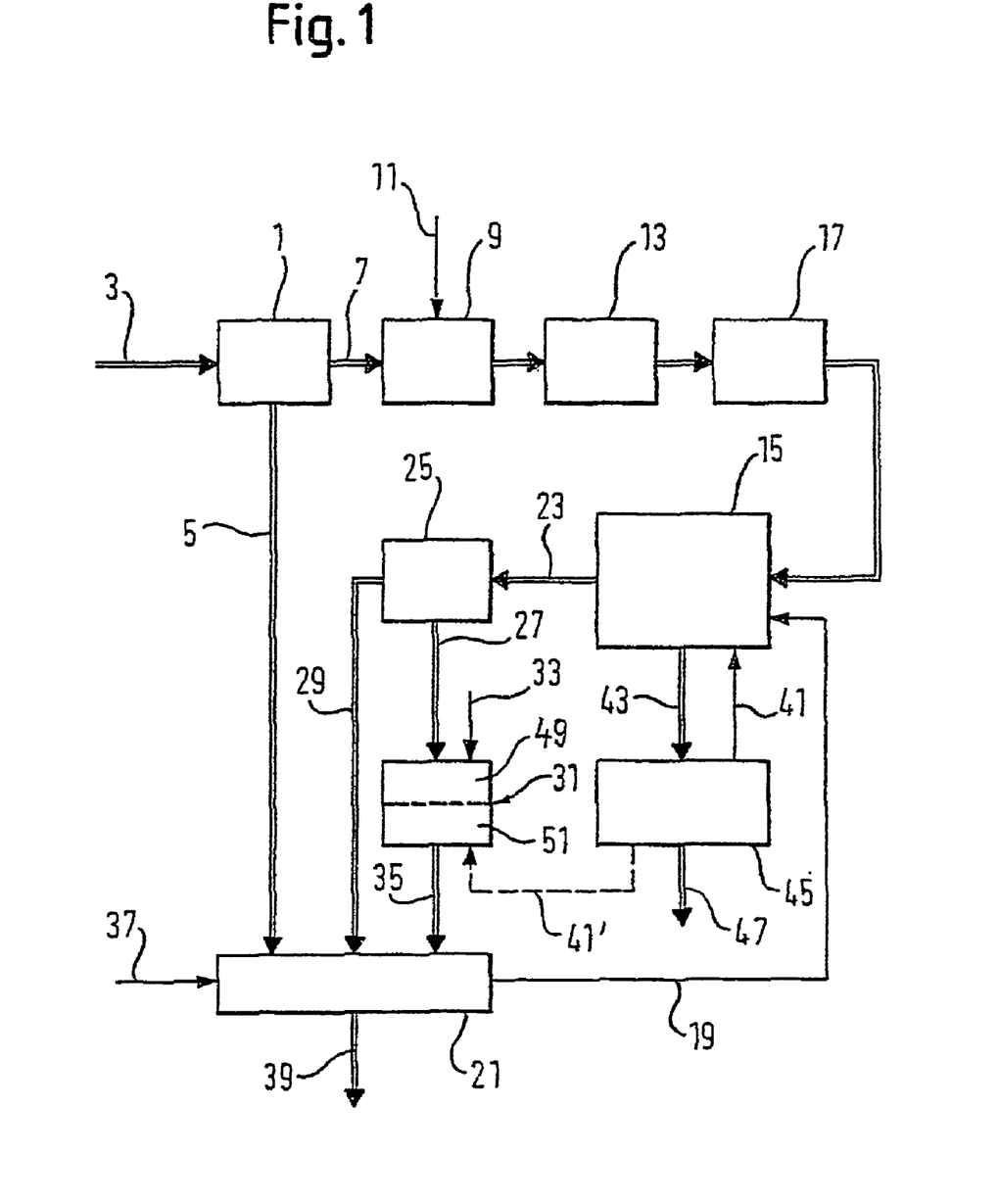
FIG. 1 shows a schematic block diagram of an inventive apparatus for producing alcohol from plant raw materials.

The apparatus shown in FIG. 1 permits dehydrated ethyl alcohol to be produced industrially from plant, carbohydrate- and/or sugar-containing raw materials, here cereals, for example cereal grains or corn, with markedly reduced energy consumption compared with conventional apparatuses. The apparatus comprises a milling station 1 which mills the cereals fed as raw material at 3 with separation of at least a part of the seed coat portions enclosing the starch- and/or sugar-containing grain to give flour of a mean particle size of greater than 0.2 mm, expediently 0.5 to 1 mm. The milling station 1 is preferably constructed as a roller mill or as an impact jet mill. Examples of mills of this type are described, for example, in "Ullmanns Encyclopädie der technischen Chemie" [Ullmann's Encyclopedia of Industrial Chemistry], third edition, 1951 Verlag Urban und Schwarzenberg, Volume 1, pages 622, 623, 633, 634. Expediently, the milling station 1 is adjusted so that it yields the seed coat portions in a weight ratio of seed coat portions to flour portion of 1:9 to 2:8 at 5 for the further use described in more detail hereinafter.

The flour delivered at 7 is, if appropriate after suspension, fed to a liquefaction station 9 in which the mostly granular starch of the flour is liquefied with addition of enzymes and thus digested into a fermentable form. The starch in this case is first heated with supply of steam 11 above the raw-material-dependent gelatinization temperature and then cooled again. The gelatinization temperatures for barley, wheat or rye are in the order of magnitude of 80° C., for corn about 75° C., and for oats 85° C. Details of the liquefaction station 9 are explained hereinafter with reference to FIG. 2.

The sweet mash produced in the liquefaction station 9, after cooling to saccharification temperature of about 60° C., is saccharified with addition of enzymes in the course of a residence time of 0.2 to 5 hours and then, after further cooling to fermentation temperature of approximately 35 to 40° C., fermented to alcohol with addition of yeast and, if appropriate, further enzymes. The saccharification step can if appropriate be omitted, in which case the sweet mash is then directly cooled to the fermentation temperature in the liquefaction station 9.

In the fermentation station 13, during the fermentation, in addition to alcohol, carbon dioxide ($CO_2$) is also produced, which in part dissolves in the mash produced in the fermentation. The $CO_2$ prevents the function of distillation columns of a distillation station 15 in which the alcohol produced by fermentation in the mash is separated off. The mash is therefore fed to the distillation station 15 via a degassing station 17 in which the $CO_2$ dissolved in the mash is separated off and in addition the mash is defoamed. Details of the degassing station are explained hereinafter on the basis of FIG. 3.

In the distillation station 15 the mash is heated with, as is explained in more detail hereinafter, the majority of the energy required therefor is recovered from the waste heat of other process stages, in particular the exhaust vapor 19 of a drier 21 which finishes drying of the vinasse which is produced as residue of the distillation process at 23 to give a dry end product (DDGS) usable as animal feed owing to its high protein content. The vinasse produced at 23 is first divided in a separator 25, for example a decanter, into a thin-juice product stream 27 and a solids product stream (wet cake) 29. The thin-juice product stream 27 is first evaporated in an evaporator 31 with supply of energy 33 to give a thick-juice product stream 35 and then the thick-juice product stream 35 and the solids product stream 29 are fed together with the seed coat portion product stream 5 separated off in the milling station 1 to the drier 21 which is heated by external energy 37 for the final drying. The resultant dried vinasse is produced at 39. Details of the production of dried vinasse are described, for example, in the publication "Die Branntweinwirtschaft" May 1976, pages 138 to 141.

The exhaust vapor produced in the drier has a dew point temperature of above 95° C., preferably 100 to 105° C., and therefore operates essentially in an air-free manner. Suitable driers are, in particular, superheated steam driers or trickle driers, as are described, for example, in said literature reference "Ullmanns Encyclopädie der technischen Chemie" [Ullmann's Encyclopedia of Industrial Chemistry], pages 577 and 601. The drier 21 produces in this manner exhaust vapor having a temperature permitting the distillation of the alcohol in the distillation station 15.

The seed coat portion (bran) separated off in the milling station 1 is fed directly to the drier 21, that is to say is not subjected to the liquefaction and need not be dried again after the mashing. The seed coat portion of the raw material serves rather in the drier 21 as carrier material for the solids-product stream 29 and also the thick-juice product stream 35. In this manner the proportion of dried vinasse which in conventional drying methods is recirculated for the drying process as carrier material can be reduced. The drier 21 can thus be made smaller, and the energy requirement or steam consumption of the drier 21 is decreased. The removal of the seed coat portions at 5 in the milling station 1, furthermore, increases the starch content in the flour actually fed to the liquefaction, which increases the achievable alcohol content of the mash in the fermentation in the fermentation stage 13 and thus decreases the energy consumption in the distillation of the mash.

The size reduction which is described above of the drier 21 can, in individual cases, lead to the waste steam heat utilized for the distillation process of the distillation stage 15 not being sufficient to be able to carry out the entire distillation process. As will further be explained in detail on the basis of FIG. 4, to cover any energy deficit, the waste heat of a dehydration stage 45 receiving the crude alcohol of the distillation station 15 at 43 can be covered. The dehydration stage 45 is preferably constructed as a molecular sieve and delivers the dehydrated ethyl alcohol as end product at 47. The molecular sieve is operated in this case at a pressure of at least 1.7 bar absolute to achieve a utilizable waste heat temperature in the distillation process of above 90° C.

In the event that the process heat of the distillation stage 15 can already be covered solely by the drier 21, the waste heat of the dehydration station 45 can be used in other ways in the alcohol production process. An advantageous utilization is possible in the evaporator 31 in vinasse drying. The evaporator 31 comprises for this purposes a pre-evaporator 49 which is operated, for example, with live steam, but preferably with mechanical vapor compression, which pre-evaporator pre-concentrates the solids fraction in the vinasse thin juice influent at 27 to 17% to 24%, while a final evaporator 51 connected downstream in the product stream ensures further concentration of the solids fraction to 25% to 50%, depending on raw material or enzymes added. If the waste heat energy of the dehydration station 45 is not required in the distillation station 15, it can, as shown at 41', alternatively be utilized to heat the final evaporator 51. For this, only the pre-evaporator 49 needs to be heated by the electrical energy fed to the evaporator 31 at 33 in the case of mechanical vapor compression. Details of the final evaporator 51 are explained hereinafter on the basis of FIG. 5.

Figure 2:
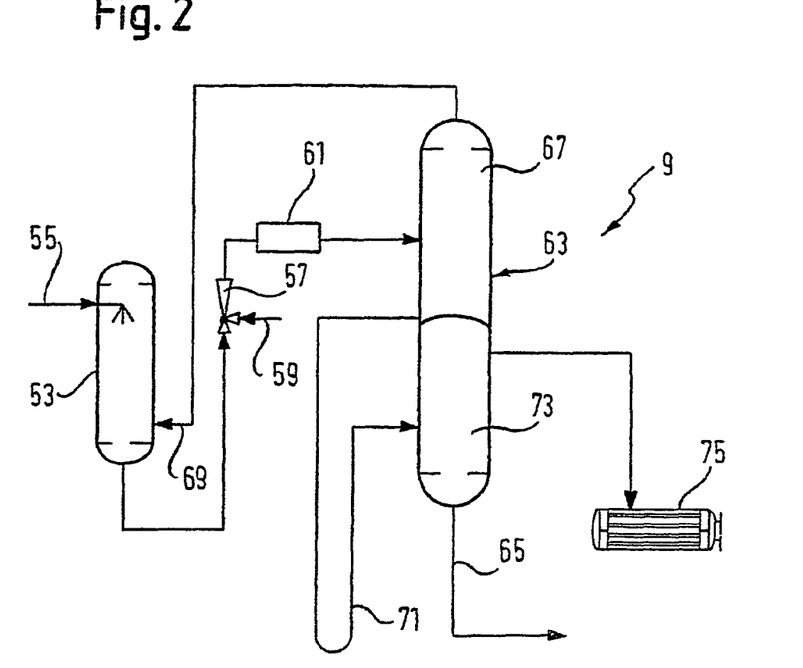
FIG. 2 shows a schematic block diagram of a liquefier station of the apparatus.

FIG. 2 shows details of the liquefaction station 9. This comprises a mixing condenser 53 which, at 55, heats the flour from the milling station 1, if appropriate in suspended form, and admixed with enzymes required for the liquefaction to a temperature below the gelatinization temperature of the raw material utilized for the alcohol production. The product which is preheated in this way is mixed with live steam 59 in a steam-jet injector 57 and as a result heated to a temperature above the gelatinization temperature of the raw material and fed to a residence time section 61 in which it is kept above the gelatinization or liquefaction temperature for a certain time of, for example, 0.1 to 1 hour. Thereafter, the liquefied product is cooled in a multistage expansion cooler 63 to the temperature required for the further processing of the sweet mash which arises at the exit 65. The expansion vapor arising in the first stage 67 of the expansion cooler 63 is fed immediately at 69 to the mixing condenser 53. Heat recovery by this means is therefore possible, but without heat-transfer surfaces which have a tendency toward encrustation having to be used. The second expansion stage 73 of the expansion cooler 63 which is connected via a pressure equilibration siphon 71 to the first expansion stage 67 of the expansion cooler 63 and which delivers sweet mash at 65 feeds its expansion vapor to a heat exchanger 75 for heat recovery in other ways.

The mixing condenser 53 heats the product to a few degrees Celsius below the gelatinization temperature, so that the steam-jet injector can increase the product temperature to a few degrees above the gelatinization temperature with comparatively low steam consumption. The energy consumption of the mixing condenser 53 can in this case be completely covered by the expansion vapor of the expansion cooler 9.

In the present exemplary embodiment, only the expansion cooler 9 is constructed so as to be multistage. Of course, the mixing condenser 53 can also have a plurality of stages each of which is then separately supplied with expansion steam via individually assigned stages of the expansion cooler.

Figure 3:
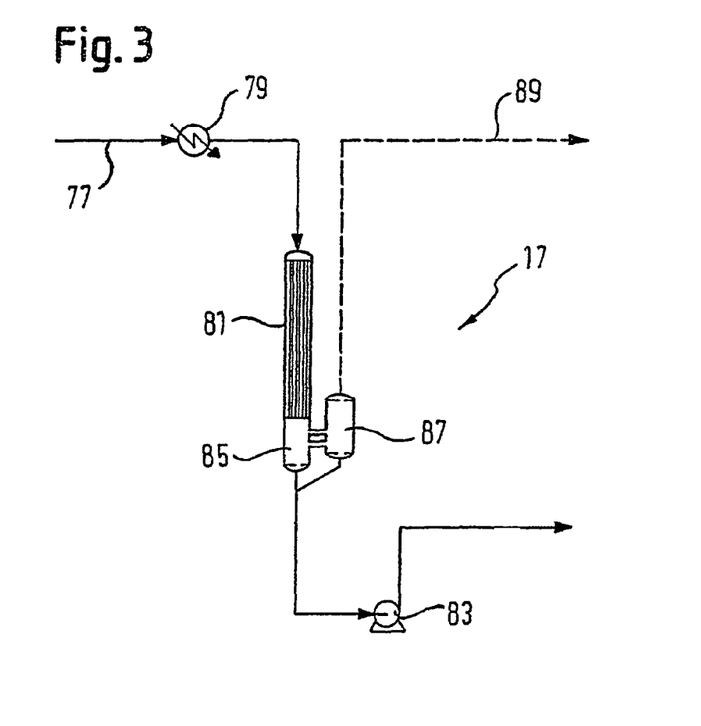
FIG. 3 shows a schematic block diagram of a degassing station of the apparatus.

FIG. 3 shows details of the degassing station 17. The alcohol-containing mash fed at 77 from the fermentation station 13 is first preheated in a heat exchanger 79 and then atomized at the top end of a tube-bundle expander 81 which stands vertically with its tube bundle 81 so that it can expand in the tubes before the degassed mash is taken off by a discharge pump 83 from the bottom phase connecting to the bottom end of the tube bundle and is fed to the distillation station 15. The bottom phase 85 forms a first separator which communicates with a laterally arranged liquid separator 87. The liquid separator 87 is connected at 89 to a vacuum system which takes off $CO_2$ and also water vapors and alcohol vapors. The arrangement is such that a reduced pressure is formed at the bottom end of the tube bundle and the mash flows through the tube bundle at a speed of about 20 to 60 m/s. This promotes the degassing of the mash and ensures, in particular, that the vapor produced in the expansion disintegrates the foam of the mash. Since the mash is degassed, the distillation column of the distillation station 15 which is explained hereinafter can be constructed more simply and the vacuum system of the distillation column also simplifies. This is also accompanied by a reduction of the pressure drop in the distillation column.

Figure 4:
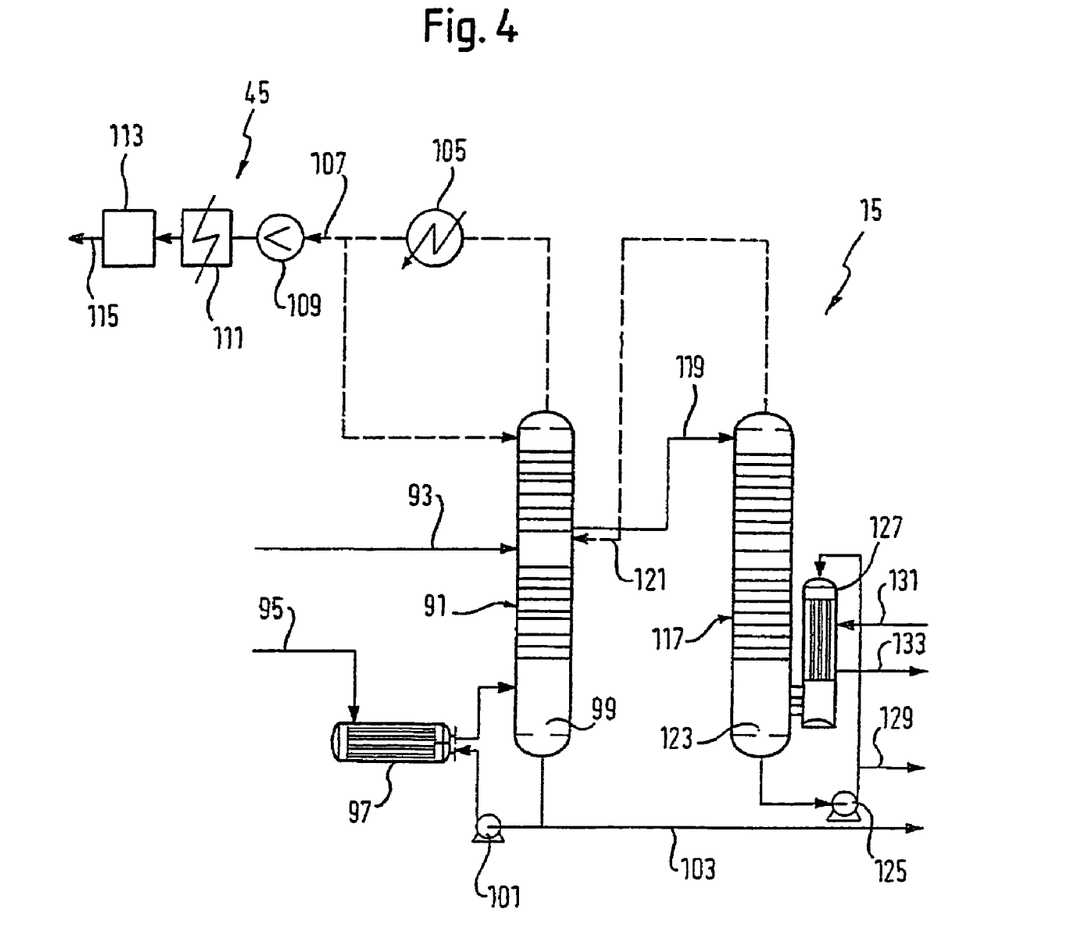
FIG. 4 shows a schematic block diagram of a distillation station together with a subsequent dehydration station of the apparatus and FIG. 5 shows a schematic block diagram of a final evaporator provided in the apparatus according to FIG. 1 for vinasse drying.

Details of the distillation station 15 are shown in FIG. 4. The distillation station 15 comprises a first rectification or distillation column 91 to which is fed the degassed mash from the degassing station 17 at an intermediate level at 93. The exhaust vapor of the drier 21 which is fed at 95 feeds a heat exchanger 97 which, by means of a circulation pump 101, circulates and heats the vinasse which collects in the bottom 99 of the distillation column 91. Furthermore, the vinasse which is fed to the separator 25 for the drying operation is taken off from the bottom 99 at 103. In the upper region of the distillation column 91, alcohol- and water-containing vapor-liquid mixture is circulated in a conventional manner via a condenser 105 and taken off by means of a pump 109 at 107 as water-containing crude alcohol. The crude alcohol taken off is heated in an evaporator 111 to a temperature above 90° C. and fed under the pressure of the pump 109 to a molecular sieve 113 forming the dehydration station 45. The molecular sieve 113 dehydrates the crude alcohol and, at 115, delivers anhydrous ethyl alcohol as end product of the alcohol production. It is essential that the pump 109 elevates the pressure in the molecular sieve 113 to more than 1.7 bar absolute in order to be able to utilize in this manner the product stream of dehydrated alcohol vapor which is available at 115 for the waste heat recovery in a manner still to be explained in more detail hereinafter.

Whereas the distillation column 91 is supplied exclusively with process heat from the waste heat of the drier 21, a second distillation column 117 which is connected to the distillation column 91 in the manner of a "side stripper", is essentially supplied exclusively with process heat by the waste heat of the dehydrated alcohol vapor exiting from the molecular sieve 113. The distillation column 117 withdraws an alcohol/water mixture at a level above the mash feed level 93 of the distillation column 91, which alcohol/water mixture is fed at 119 to the top of the distillation column 117 and, after alcohol enrichment, is recirculated to the distillation column 91 at a somewhat lower level at 121. The essentially mash-free bottom phase 123 of the distillation column 117 comprises first-runnings water which is circulated by means of a circulation pump 125 through a falling-film evaporator 127, so that water can be taken off from the distillation column 117 at 129. The falling-film evaporator 127 is heated by the water-free alcohol vapor from the molecular sieve 113, which water-free alcohol vapor is heated to at least 90° C., the water-free alcohol vapor being fed at 131 and being removed at 133 as cooled end product of the alcohol production apparatus. Examples of suitable falling-film evaporators are described, for example, in CH 510 450 or DE 1 519 714 A. An example of a molecular sieve is described in U.S. Pat. No. 4,407,662.

Figure 5:
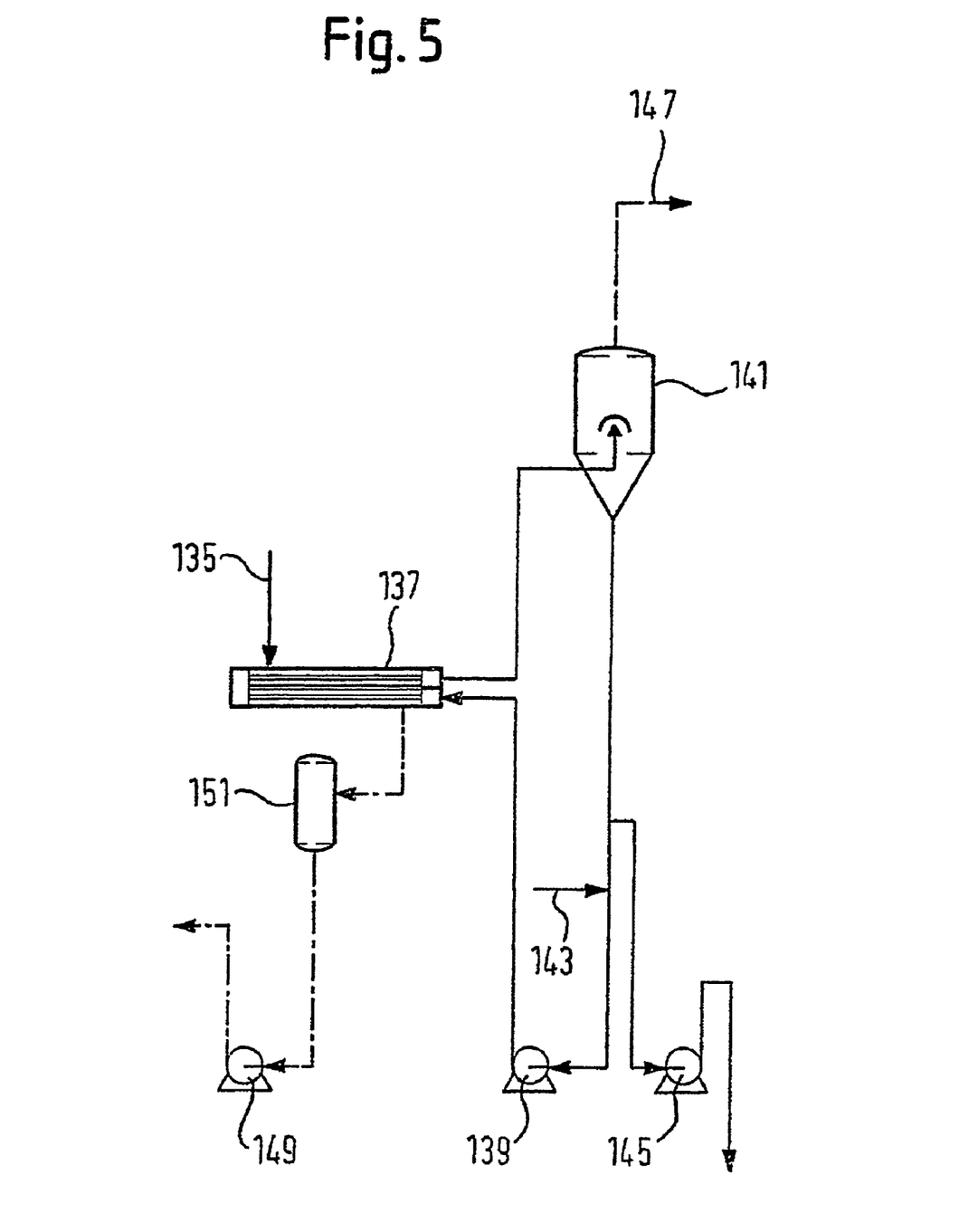

The distillation station 15 explained above can, owing to the heat recovery from the product stream of the dehydrated ethyl alcohol, be operated even when the drier 21, in the event of size reduction of the drier capacity because of the feed of the bran or seed coat portion of the raw material separated off in the milling station, supplies insufficient energy for operating the entire distillation process. However, if the waste heat of the drier 21 is sufficient, the waste heat of the molecular sieve 113 can also be recovered in other ways, in particular as process heat in the final evaporator 51.

As FIG. 5 shows, the ethanol vapor which is dehydrated in the molecular sieve 113 at a temperature of above 90° C. and a pressure of greater than 1.7 bar absolute, is fed at 135 to a heat exchanger 137 constructed as a forced-circulation evaporator heater and heats there the vinasse juice which is preconcentrated in the pre-evaporator 49 and fed at 143 to the evaporator circuit and circulated by a circulation pump 139 through the heat exchanger 137 and expansion vessel 141. A discharge pump 145 withdraws the thick vinasse juice at a point in the circuit upstream of the juice feed 143 and passes it to the drier 21. Water vapor produced in the expansion vessel 141 is fed at 147 to a condensation system or further evaporator not shown in more detail. The dehydrated alcohol vapor which is cooled in heat exchanger 137 is removed as end product of the alcohol production by means of a discharge pump 149 which, if appropriate, is connected via a compensation or receiver vessel 151 to the heat exchanger 137.

The invention claimed is:

1. An apparatus for producing alcohol from cereal raw materials, comprising
    a grinding station (1) comprising a separator and a feeder, wherein said grinding station is configured to grind grain comprising a starch and/or sugar of the cereal raw materials to flour, said separator is configured to separate at least a part of seed coat portions enclosing said grain, and said feeder is configured to feed said separated dry seed coat portions directly from said grinding station to a dryer, wherein said dry seed coat portions function as a carrier medium for vinasse,
    a liquefaction station (9) which digests flour to a liquefied raw material,
    a fermentation station (13) which ferments said liquefied raw material to mash,
    a distillation station (15) comprising a distillation column (91) for separating off alcohol from the mash, and
    a drying station (21, 31) configured to dry vinasse produced as a residue in said distillation station at a dew point temperature of above 95° C., comprising a dryer producing exhaust vapor having a temperature permitting the distillation of said alcohol in said distillation station, wherein said drying station contains said dry seed coat portions as the carrier medium.

2. The apparatus as claimed in claim 1, characterized in that the grinding station (1) separates off the seed coat portions in a weight ratio of seed coat portions to flour of 1 to 9 to 2 to 8.

3. The apparatus as claimed in claim 1, characterized in that the grinding station (1) grinds the cereals to flour with a mean particle size between 0.5 and 1 mm.

4. The apparatus as claimed in claim 1, characterized in that the grinding station (1) has a roller mill or an impact jet mill.

5. The apparatus as claimed in claim 1, wherein said liquefaction station (9) comprises at least one mixing stage comprising a mixing condenser (53) for admixing steam to a product stream of the ground cereal raw material or a suspension thereof, a steam-jet injector (57) downstream of the mixing condenser (9) for admixing superheated steam to the product stream, and an expansion cooler (63) for the product stream connected downstream of the steam-jet injector (57) and comprises at least one expansion stage (67, 73), said mixing condenser (53) admixing expansion vapor of said expansion cooler (63) to said product stream.

6. The apparatus as claimed in claim 5, wherein said expansion cooler (63) is of multistage construction.

7. The apparatus as claimed in claim 6, characterized in that the mixing condenser (53) is of single-stage construction, and the expansion cooler (63) is of two-stage construction.

8. The apparatus as claimed in claim 5, characterized in that the mixing condenser (53) heats the product stream to a temperature below the gelatinization temperature of the raw material, and the steam-jet injector (57) heats the product stream to a temperature above the gelatinization temperature of the raw material.

9. The apparatus as claimed in claim 1, characterized in that, between the fermentation station (13) and the distillation station (15), there is disposed a degassing station (17) in which the mash product stream passes through from top to bottom a vertically standing tube bundle (81) which is evacuated at its bottom end, and the mash product stream expands in the tube bundle (81).

10. The apparatus as claimed in claim 9, characterized in that the mash product stream, before entry into the tube bundle (81), passes through a heat exchanger (79) preheating the mash.

11. The apparatus as claimed in claim 1, wherein said dryer (21) produces essentially air-free exhaust vapor.

12. The apparatus as claimed in claim 1, wherein said dryer (21) is constructed as a superheated steam dryer.

13. The apparatus as claimed in claim 1, characterized in that the distillation station (15) has a first distillation column (91) which is heated, in particular, by exhaust vapor of the drying station (21, 31), to which is connected a dehydration station (45) which dehydrates its crude alcohol product stream
and in that a second distillation column (117) is connected at an intermediate level of the first distillation column (91) above its mash feed level (93), which second distillation column is heated via a heat exchanger (127) by heat of the dehydrated alcohol vapor of the dehydration station (45).

14. The apparatus as claimed in claim 13, characterized in that the heat exchanger is constructed as a falling-film evaporator (127) heated by dehydrated alcohol vapor of the dehydration station (45).

15. The apparatus as claimed in claim 13, characterized in that the dehydration station (45) comprises a molecular sieve (117).

16. The apparatus as claimed in claim 15, characterized in that the molecular sieve (117) is operated at a pressure of 1.7 bar absolute or more.

17. The apparatus as claimed in claim 1, characterized in that the drying station (21, 31) comprises a separator (25) which separates the vinasse into a vinasse-thin juice product stream and a vinasse-solids product stream, an evaporator (31) which evaporates the vinasse-thin juice product stream to form vinasse-thick juice, and also a dryer (21) which dries the vinasse-thick juice together with the vinasse-solids to give dry vinasse,
in that the distillation station (15) is connected downstream of the dehydration station (45) which dehydrates the crude alcohol product stream
and in that the evaporator (31) has at least one evaporator stage (51) heated by heat of the dehydrated alcohol vapor of the dehydration station.

18. The apparatus as claimed in claim 17, characterized in that the evaporator (31) comprises a pre-evaporator (49) and a final evaporator (51) and in that the final evaporator (51) is heated by dehydrated alcohol vapor from the dehydration station (45).

19. The apparatus as claimed in claim 17, characterized in that the dehydration station (45) comprises a molecular sieve (117).

20. The apparatus as claimed in claim 19, characterized in that the molecular sieve (117) is operated at a pressure of 1.7 bar absolute or more.

21. The apparatus of claim 1, wherein said final drying of the vinasse is carried out at a dew point temperature of from 100° C. to 105° C.

22. The apparatus of claim 1, further comprising a conduit for exhaust vapor connecting said drying station to said distillation station.

23. The apparatus of claim 1, wherein the distillation column is supplied exclusively with process heat from the exhaust vapor of the dryer.

24. A process for producing alcohol from cereal raw materials, comprising the steps of
    grinding grain comprising a starch and/or sugar of the cereal raw materials to flour;

separating at least a part of seed coat portions enclosing said grain;

liquefying said flour with addition of enzymes;

digesting said liquefied flour into a fermentable liquefied raw material;

fermenting said liquefied raw material to form a mash and alcohol;

providing a distillation station for separating said alcohol from said mash;

distilling said alcohol in said distillation station comprising a distillation column;

forming vinasse as a residue in said distillation station;

feeding said seed coat portions after said grinding and separating steps to a dryer, wherein said seed coat portions serve as carrier material for said vinasse to be dried in said dryer;

drying a vinasse-seed coat mixture in a drying station at a dew point temperature of above 95° C. producing exhaust vapor having a temperature permitting the distillation of alcohol in said distillation station; and heating said distillation station with said exhaust vapor, wherein the temperature of said exhaust vapor permits distillation in said distillation column exclusively with said exhaust vapor.

25. The process of claim 24, wherein said cereals are ground to flour with a mean particle size between 0.5 and 1 mm.

26. The process of claim 24, wherein said grinding is performed by a roller mill or an impact jet mill.

27. The process of claim 24, further comprising at least one mixing stage.

28. The process of claim 24, further comprising admixing superheated steam to said vinasse.

29. The process of claim 24, wherein the mash is degassed prior to distillation.

30. The process of claim 24, further comprising heating said mash in a heat exchanger.

31. The process of claim 24, wherein said exhaust vapor is essentially air-free.

32. The process of claim 24, wherein said drying is performed in a superheated steam dryer.

33. The process of claim 24, further comprising dehydrating said alcohol in a dehydration station.

34. The process of claim 24, wherein the distillation station comprises a first distillation column heated by exhaust vapor produced in said drying station, and a second distillation column connected at an intermediate level of the first distillation column, wherein said second distillation column is heated via a heat exchanger by heat of dehydrated alcohol vapor.

35. The process of claim 34, wherein the heat exchanger is a falling-film evaporator heated by dehydrated alcohol vapor.

36. The process of claim 24, further comprising the step of separating the vinasse into a vinasse-thin juice product stream and a vinasse-solids product stream.

37. The process of claim 36, further comprising evaporating said vinasse-thin juice product stream is to form a vinasse-thick juice.

38. The process of claim 24, wherein said seed coat portions are in a weight ratio of between 1:9 and 2:8 to said flour.

39. An apparatus for producing alcohol from a cereal grain raw material, comprising grinding means for grinding said cereal grain raw material into a flour and separating at least a part of a seed coat portion enclosing said cereal grain raw material, liquefying means for digesting said flour into a liquefied raw material, fermenting means for fermenting said liquefied raw material to form a mash, distillation means comprising a distillation column for separating alcohol from said mash at a dew point temperature of above 95° C., drying means comprising a dryer for drying a vinasse formed as a residue in said distillation means and for producing an exhaust vapor for heating said distillation column, and feeding means for feeding dry seed coat portions from said grinding means to said dryer, wherein said dry seed coat portions serve as a carrier medium for said vinasse.

40. The apparatus as claimed in claim 1, wherein said dry seed coat portions are not subjected to said liquefaction station prior to being fed to the dryer.

41. The apparatus as claimed in claim 39, wherein said dry seed coat portions are not subjected to said liquefying means prior to being fed to said dryer by said feeding means.

42. The process of claim 24, wherein said dry seed coat portions are not subjected to liquefaction prior to being fed to the dryer.

43. The process of claim 24, wherein said dry seed coat portions are not dried after completion of the fermenting said liquefied raw material to form a mash and alcohol and prior to being fed to the dryer.

* * * * *